United States Patent
Ho et al.

(10) Patent No.: US 8,530,220 B2
(45) Date of Patent: Sep. 10, 2013

(54) MICROORGANISMS, MICROBIAL PHOSPHATE FERTILIZERS AND METHODS FOR PREPARING SUCH MICROBIAL PHOSPHATE FERTILIZERS

(75) Inventors: Biu Ho, Foshan (CN); En-hsiung Huang, Foshan (CN); Ting Kwok Ho, Foshan (CN); Ting Wing Ho, Foshan (CN)

(73) Assignee: Foshan Jinkuizi Plant Nutriment Co., Ltd. (CN)

( * ) Notice: Subject to any disclaimer, the term of this patent is extended or adjusted under 35 U.S.C. 154(b) by 539 days.

(21) Appl. No.: 12/744,846

(22) PCT Filed: Nov. 6, 2008

(86) PCT No.: PCT/CN2008/001850
§ 371 (c)(1),
(2), (4) Date: Oct. 21, 2010

(87) PCT Pub. No.: WO2009/070966
PCT Pub. Date: Jun. 11, 2009

(65) Prior Publication Data
US 2011/0100078 A1 May 5, 2011

(30) Foreign Application Priority Data
Nov. 26, 2007 (CN) .......................... 2007 1 0093104

(51) Int. Cl.
*C12N 1/20* (2006.01)
*C05F 11/08* (2006.01)

(52) U.S. Cl.
USPC ............................... 435/243; 435/252.4; 71/8

(58) Field of Classification Search
None
See application file for complete search history.

(56) References Cited

FOREIGN PATENT DOCUMENTS

CN      1417167 A   *   5/2003
CN    101225367 A      7/2008

OTHER PUBLICATIONS

Banik, S. et al. Effect of inoculation with native phosphate solubilizing microorganisms on the available phophorus content in the rhizosphere and uptake of phosphorus by rice plants grown in an Indian alluvial soil. Zentralblatt fur Mikrobiologie (1985) 140:455-464.*
International Search Report for International Application No. PCT/CN2008/001850 with English translation mailed Jan. 22, 2009.

* cited by examiner

*Primary Examiner* — John S. Brusca
*Assistant Examiner* — Sharon M Papciak
(74) *Attorney, Agent, or Firm* — Cantor Colburn LLP

(57) ABSTRACT

The present invention relates to a microorganism, a microbial phosphate fertilizer and a method for manufacturing the microbial phosphate fertilizer, wherein the microorganism is *Streptomyces cellulosae* with Accession number CGMCC No. 2167 or *Aspergillus versicolor* with Accession number CGMCC No. 2171. The microbial phosphate fertilizer of the present invention comprises a fermentation product of the microbial composition consisting of the following four microorganisms: *Bacillus subtilis* strain WH2, *Bacillus licheniformis* strain WH4, *Streptomyces cellulosae* strain WH9 and *Aspergillus versicolor* strain WH13. A method for manufacturing the microbial phosphate fertilizer is also provided, wherein the manufacture of the microbial phosphate fertilizer may involve the use of ground phosphate rock having 8%-12% $P_2O_5$.

7 Claims, No Drawings

MICROORGANISMS, MICROBIAL PHOSPHATE FERTILIZERS AND METHODS FOR PREPARING SUCH MICROBIAL PHOSPHATE FERTILIZERS

This is a U.S. national stage application of International Application No. PCT/CN2008/001850, filed on 6 Nov. 2008. Priority under 35 U.S.C. §119(a) and 35 U.S.C. §365(b) is claimed from Chinese Application No. CN 200710093104.1, filed 26 Nov. 2007, the disclosure of which is also incorporated herein by reference.

FIELD OF THE INVENTION

The present invention relates to the field of microbial fertilizers, especially to novel microorganisms, microbial phosphate fertilizers obtained from the fermentation products of the microbial composition comprising said microorganisms, and the method for manufacturing said microbial phosphate fertilizers.

BACKGROUND OF THE INVENTION

Conventional phosphate fertilizers are produced by chemical methods, that is, by decomposition of phosphate rock using concentrated sulfuric acid to produce phosphate fertilizers of high solubility. Sulfides such as sulfur dioxide, generated in the process of manufacturing the phosphate fertilizers, release to the atmosphere and lead to air pollution, sulfates originated from the use of phosphate fertilizers causes soil acidification, and 70% or more of phosphate ions are immobilized by elements like aluminium, iron, calcium and magnesium in soil, resulting in soil salinization. Typically, less than 30% of phosphorus in soil is substantively used by crops (plants) indeed.

The grade of phosphate rock is classified by its content (in percentage) of $P_2O_5$. Generally speaking, phosphate rock having more than 28% $P_2O_5$ is classified as medium to high grade; phosphate rock having 8% to 28% $P_2O_5$ is classified as medium to low grade. Currently, medium to high graded phosphate rock is used as the raw material for manufacturing phosphate fertilizers by chemical method, while the cost for processing in the manufacture of the chemical phosphate fertilizers using medium to low graded phosphate rock is too high and thus medium to low graded phosphate rock is not suitable for such preparation. Taking phosphate rock having 32% $P_2O_5$ as an example, the phosphorus content contained in the chemical phosphate fertilizers produced by the decomposition of phosphate rock using concentrated sulfuric acid is about 16%. If low graded phosphate rock is used, the cost for raw materials such as phosphate rock and concentrated sulfuric acid as well as the cost for electricity consumption during the manufacture of phosphate fertilizers would be greatly increased.

Medium to low graded phosphate rock constitutes a considerable proportion of the resources for phosphate rock. In order to take full advantage of the resources for phosphate rock, to minimize the waste of the resources and to relieve the contradiction between supply and demand of the phosphate fertilizers, full utilization of the medium to low graded phosphate rock which is not suitable for preparing phosphate fertilizers is of significant importance.

There are many problems with the conventional use of phosphate rock in the manufacture of chemical phosphate fertilizers, which includes: 1) liquid waste of sulfur dioxide and strong acids caused by the plenty use of strong acids for the decomposition of ground phosphate rock in the manufacture of phosphate fertilizers leads to pollutions of air, soil and water sources; 2) utilization of the resources for phosphate rock is relatively low, and that waste of resources is particularly acute on the premise of the current low production yield of the high graded phosphate rock; 3) the use of traditional phosphate fertilizers, to a great extent, causes soil acidification, which significantly constrains the sustainable development of agriculture; 4) the use of high concentrated superphosphate typed fertilizers leads to the high nitrate content in crops, from which the health of people would be suffered and their life safety would render uncertain.

Along with the development of economy and the rise of consumption standard, the desire for foods has been generally changed from quantity fed to safety and quality, and there is growing concern about food quality and its safety issues. Food (especially agricultural products) safety issues have caused wide public concern all over the world. To solve the food safety issues, the root causes should be addressed. As most of the foods for human consumption come from agricultural products, solving the problem of soil pollution, restoring the ecological environment of soil, research and development of biological phosphate fertilizers represent the important measures with promising future for ensuring food safety.

SUMMARY OF THE INVENTION

The objective of the present invention is to provide a microbial phosphate fertilizer and a method for preparing the same, wherein a group of WH microbes contained in said microbial phosphate fertilizer are phosphorus-dissolving microbes, which make use of active organic matter and ground phosphate rock as the life carriers. Said microbial phosphate fertilizer can keep the soil from packing together, facilitate the formation of soil cluster structure, enhance the soil permeability and its water storage capacity to ensure fertility, autobalance the soil acidity and basicity, improve the fertility of soil itself and the fertilizer efficiency thereof, pose positive effects on the transformation of desertified land and saline-alkali soil, prevent the occurrence of diseases caused by a variety of soil fungi and bacteria, relieve the continuous cropping stress, improve the disease resistance of crops, enable the degradation of pesticide residues in soil and improve crop quality.

Another objective of the present invention is to convert the medium to low graded ground phosphate rock to the active microbial phosphate fertilizers of high performance of the present invention by means of the microbial composition of the present invention, fully utilize the mineral resources, relieve the demand and supply pressure of phosphate rock resources, and at the same time, the active microbial phosphate fertilizer of the present invention consumes less electricity in the production process, which is energy saving and environmental friendly. The present invention provides two novel microorganisms, *Streptomyces cellulosae* named WH9 and *Aspergillus versicolor* named WH13.

The microbial phosphate fertilizer of the present invention comprises a fermentation product of the microbial composition consisting of the following four microorganisms: *Bacillus subtilis* named WH2; *Bacillus licheniformis* named WH4; *Streptomyces cellulosae* named WH9; *Aspergillus versicolor* named WH13. The depository information of WH2 and WH4 are listed as follows: *Bacillus subtilis*: depository institution: China General Microbiological Culture Collection Center of China Administration Committee for Culture Collection of Microorganisms (abbr. CGMCC), depository date: Apr. 23, 1999, accession number: CGMCC NO. 0395.2, referred to as WH2; *Bacillus licheniformis*: depository institution: China General Microbiological Culture Collection Center of China Administration Committee for Culture Collection of Microorganisms (abbr. CGMCC), depository date: Apr. 23, 1999, accession number: CGMCC NO. 395.4, referred to as WH4; *Streptomyces cellulosae*: depository institution: China General Microbiological Culture Collection Center of China Administration Committee for Culture Collection of Microorganisms (abbr. CGMCC), depository date: Sep. 13, 2007, accession number: CGMCC NO. 2167, referred to as WH9; *Aspergillus versicolor*: depository institution: China General Microbiological Culture Collection Center of China Administration Committee for Culture Collection of Microorganisms (abbr. CGMCC), depository date: Sep. 13, 2007, accession number: CGMCC NO. 2171, referred to as WH13.

The microbial phosphate fertilizer of the present invention is a fermentation product of the microbes (after $1^{st}$ cultivation of above microbial composition) with the ground phosphate rock and active organic matter. Active organic matter is one or more of the species selected from the group of the followings: filtration mud in sugar industry, chicken manure, pig manure, peanut bran, oatmeal, cassaya residue and rapeseed cake etc.

The proportion of the individual microorganisms in the microbial composition used in the microbial phosphate fertilizers of the present invention is expressed as percentage by weight (based on the total weight of the microbial composition):

| | |
|---|---|
| (1) WH2: 13-50%; | (2) WH4: 10-45%; |
| (3) WH9: 8-40%; | (4) WH13: 8-37%. |

The present invention also provides a method for preparing the above-mentioned microbial phosphate fertilizers, comprising the following steps:

(1) Mixing WH2, WH4, WH9 and WH13 according to the percentage by weight as described above, to give the microbial composition;

(2) Preparing the microbe (after $1^{st}$ cultivation) culture medium of said microbial composition according to the following percentage by weight:

Active organic matter: 35-45%; rice bran: 35-45%; soybean powder: 15-17%; milk powder: 1.5-2.5%; sugar: 0.5-1.5%; remaining water;

(3) Cultivating the microbes (after $1^{st}$ cultivation) of the microorganisms: mixing the microbe (after 1st cultivation) culture medium of the microbial composition according to the above formulation with stirring, followed by inoculating the microbial composition at room temperature, cultivating in the microbes (after 1st cultivation) culture medium at the temperature ranged from 30° C.-60° C., pH 6.5-7.5 for a period of 5-15 days, then obtaining the microbes (after 1st cultivation) of the microbial composition;

(4) Mixing ground phosphate rock, active organic matter and the microbes (after 1st cultivation) of the microbial composition according to the following percentage by weight (based on the total weight of the three components as described above), followed by fermenting at room temperature for more than 12 days, which results in the microbial phosphate fertilizers:

| | |
|---|---|
| Ground phosphate rock | 20-90%; |
| Active organic matter | 5-40%; |
| Microbes (after 1st cultivation) of the microbial composition | 5-40%. |

In general, the number of the viable microorganisms of the microbes (after 1st cultivation) of the microbial composition cultivated in step (3) is 500 million/gram to 3 billion/gram.

Medium to low graded ground phosphate rock having 8-28% $P_2O_5$ can be used as the ground phosphate rock above, from which transformation to a active microbial phosphate fertilizer of high performance via biological fermentation is achieved by which mineral resources can be fully utilized.

The present invention develops a bioactive phosphate fertilizer by means of biological engineering, in which the strong phosphorus absorption efficiency of the WH microbial composition is fully utilized. The microbial phosphate fertilizers of the present invention are formulated and obtained from pure cultivation of a variety of beneficial agricultural microbes having subjected to a strict screening process, such that phosphorus-dissolving may be achieved after being applied in soil; soil may be prevented from packing together; supply of soil nutrients may be remarkably improved, dissolution and release of the nutrients which are hardly dissolved in soil may be primarily promoted by a variety of microorganisms in the microbial composition. Said WH microorganisms release a large amount of both inorganic and organic acidic species during metabolism, by which the release and chelation of trace elements such as silicon, aluminum, iron, magnesium, molybdenum in soil is promoted, and that soil nutrient supply is also improved.

In comparison with the prior technology, the present invention possesses the following significant effects:

(1) The active microbial phosphate fertilizers of the present invention can be directly absorbed by crops in soil under the action of the WH microbial composition, the utilization rate of phosphate fertilizers is up to more than 70%, but its usage amount is less than half of the conventional phosphate fertilizers, which remarkably increases the utilization rate of the phosphate rock resources and conserves the treasure but non-renewable resources.

(2) The WH microbial composition can decompose the insoluble salts in soil, by which the soil structure may be improved, the problem of long-term deficiency of phosphorus in soil can be solved and a significant improvement in keeping the soil from packing together can be achieved.

(3) In the course of production of phosphate fertilizers, the production cost is greatly reduced and the production efficiency is remarkably improved by means of subjecting the ground phosphate rock to biological fermentation. Traditional chemical process using concentrated sulfuric acid in the manufacture of phosphate fertilizers emits a great quantity of sulfur dioxide, leading to air pollution, whereas the microbial phosphate fertilizers of the present invention produces no sulfur dioxide in the manufacture process, by which air pollution problem caused by the traditional chemical process can be completely solved.

(4) The use of the microbial phosphate fertilizers of the present invention does not lead to soil acidification, salinization, and that the ecological environment of soil and nutrient supply in soil can be significantly improved, and the quality and yield of crops can be remarkably promoted, which is particularly suitable for the production of green foods, organic foods, so as to increase the market competitive power of agricultural products.

(5) The use of the active microbial phosphate fertilizers of the present invention exhibits a remarkably effect in reducing the nitrite content in agricultural products even down to the level harmless to human health, which is beneficial to human health.

(6) The active microbial phosphate fertilizers of the present invention make use of biological fermentation in treating the ground phosphate rock, by which less electricity would be consumed in the preparation process; electric energy used is remarkably reduced compared with processes using traditional chemical phosphate fertilizers, by which power supply is relieved, making it possible for the achievement of energy conservation and environmental protection.

(7) Under the action of the WH microbial composition, the production of the biological phosphate fertilizers that differ from the traditional chemical phosphate fertilizers in the industry is not limited to the production using high graded phosphate rock (with more than 28% $P_2O_5$). It is possible to use medium to low graded phosphate rock (with about 8%-28% $P_2O_5$), especially the low graded phosphate rock resources having less than 26% $P_2O_5$ for the production of the present biological phosphate fertilizers, which helps in solving the problem of shortage of phosphate rock resources to a great extent. Therefore, massive promotion of the use of active microbial phosphate fertilizers of the present invention can greatly increase the utilization rate of phosphate rock resources, and the effect is particularly outstanding in the case where the storing capacity of the medium to high graded phosphate rock is getting less.

(8) The use of the biological method of the present invention in the production of phosphate fertilizers allows a full utilization of the medium to low graded ground phosphate rock in its conversion into active biological phosphate fertilizers of high efficiency, by which conservation of resources and large-scale mechanized production can be achieved, which can remarkably reduce the production cost, improve the production efficiency, facilitate the virtuous cycle for sustainable resources and industry and agriculture. After subjecting to the technical treatment of biological phosphorus, the phosphorus in the phosphate rock is activated, and the use of the fertilizers according to the present invention in soil can improve the soil acidity, supplement phosphorus, improve the fertilizer efficiency, and further improve the utilization rate of resources; the active phosphate fertilizers obtained according to the present invention can remarkably increase the yield and quality of crops, and replace the chemical method for preparing phosphate fertilizers.

(9) The process for preparing the active microbial phosphate fertilizers of the present invention involves no strong acids, but involves biological fermentation instead, by which environmental pollution can be prevented; in the course of preparing the biological phosphate fertilizers, the use and operation of lots of large-scale machines and equipment is reduced, which indirectly reduces the energy consumption caused by the use of said machines and equipment, production of the biological phosphate fertilizers of the present invention can solve the problem of greenhouse effect caused by the emission of large quantity of harmful gases, to which the international community is of great concern.

The depository institution, address, depository date and accession number of the sample of the biological materials of the present invention, as well as the nomenclature by classification of said biological materials are listed in the following table:

| Depository institution | Address | Depository date | Accession number | Nomenclature by classification |
|---|---|---|---|---|
| China General Microbiological Culture Collection Center of China Administration Committee for Culture Collection of Microorganisms (abbr. CGMCC) | Institute of Microbiology, Chinese Academy of Sciences, Daitun Road, Chaoyang District, Beijing | Apr. 23, 1999 | CGMCC NO. 0395.2 | Bacillus subtilis |
| China General Microbiological Culture Collection Center of China Administration Committee for Culture Collection of Microorganisms (abbr. CGMCC) | Institute of Microbiology, Chinese Academy of Sciences, Daitun Road, Chaoyang District, Beijing | Apr. 23, 1999 | CGMCC NO. 0395.4 | Bacillus licheniformis |
| China General Microbiological Culture Collection Center of China Administration Committee for Culture Collection of Microorganisms (abbr. CGMCC) | Institute of Microbiology, Chinese Academy of Sciences, Daitun Road, Chaoyang District, Beijing | Sep. 13, 2007 | CGMCC NO. 2167 | Streptomyces cellulosae |
| China General Microbiological Culture Collection Center of China Administration Committee for Culture Collection of Microorganisms (abbr. CGMCC) | Institute of Microbiology, Chinese Academy of Sciences, Daitun Road, Chaoyang District, Beijing | Sep. 13, 2007 | CGMCC NO. 2171 | Aspergillus versicolor |

PREFERRED EMBODIMENTS OF THE INVENTION

The present invention will be further described with reference to the following examples.

Example 1

The proportion of microbial composition of the example is as follows (in percentage by weight):

| | |
|---|---|
| (1) Strain WH2: 13%; | (2) Strain WH4: 10%; |
| (3) Strain WH9: 40%; | (4) Strain WH13: 37%. |

The microbial phosphate fertilizers of the present invention are prepared according to the following steps:

(1) Mixing homogenously strains WH2, WH4, WH9 and WH13 according to the above proportion (in percentage by weight) to give the WH microbial composition;

(2) Preparing the culture medium for the 1$^{st}$ cultivation of said microbial composition according to the following percentage by weight:

Active organic matter: 40% (filtration mud: 20%, chicken manure: 20%), rice bran: 40%, soybean powder: 16%, milk powder: 2%, sugar: 1%, remaining water;

(3) Cultivating the microbes (after 1st cultivation) of the microorganisms: mixing the culture medium (step 2) of the microbial composition according to said formulation with stirring, followed by inoculating the microbial composition at room temperature, cultivating in the culture medium at the temperature of 60° C., pH 7.0 for a period of 5 days, resulting in the microbes (after 1st cultivation) of the microbial composition (or referred to as microbe inside the bran) upon the completion of cultivation; the active microorganisms contained is up to 3 billion/gram;

(4) Mixing ground phosphate rock, active organic matter and the microbes (after 1st cultivation) of the microbial composition according to the following formulation, then fermenting at room temperature for 12 days, resulting in the microbial phosphate fertilizers, which was then subjected to crushing and packing:

| | |
|---|---|
| Ground phosphate rock | 20%; |
| Active organic matter (filtration mud: 20%, chicken manure: 20%) | 40%; |
| Microbes (after 1st cultivation) | 40%. |

Example 2

The proportion and parameters of various components in the microbial phosphate fertilizer of the example are different from that of example 1 as follows:

1. The proportion (percentage by weight) of the microorganisms present in the microbial phosphate fertilizers of the present invention is:

| | |
|---|---|
| (1) Strain WH2: 50%; | (2) Strain WH4: 26%; |
| (3) Strain WH9: 8%; | (4) Strain WH13: 16%. |

2. The proportion (percentage by weight) of the culture medium for the 1$^{st}$ cultivation is as follows:

Active organic matter: 35% (filtration mud: 20%, cassaya residue: 15%), rice bran: 45%, soybean powder: 15%, milk powder: 2.5%, sugar: 1.5%, remaining water.

3. The temperature of the culture medium: 45° C., pH: 6.5, cultivation period: 10 days, active microorganisms contained: up to 1.5 billion/gram.

4. Medium to low graded ground phosphate rock, active organic matter and the microbes (after 1st cultivation) of the microorganisms are mixed according to the following formulation, and subjected to fermentation at room temperature for 13 days, resulting in the microbial phosphate fertilizers, which was then subjected to crushing and Packing:

| | |
|---|---|
| Ground phosphate rock | 55%; |
| Active organic matter (peanut bran: 10%, pig manure: 10%) | 20%; |
| Microbes (after 1st cultivation) | 25%. |

The proportion and parameters of other components and process step are the same as Example 1.

Example 3

The proportion and parameters of various components in the microbial phosphate fertilizer of the example are different from that of example 1 as follows:

1. The proportion (percentage by weight) of the microorganisms present in the microbial phosphate fertilizers of the present invention is:

| | |
|---|---|
| (1) Strain WH2: 30%; | (2) Strain WH4: 45%; |
| (3) Strain WH9: 17%: | (4) Strain WH13: 8%. |

2. The proportion (percentage by weight) of the culture medium for the 1$^{st}$ cultivation is as follows:

Active organic matter: 45% (filtration mud: 30%, pig manure: 15%), rice bran: 35%, soybean powder: 15%, milk powder: 1.5%, sugar: 1.5%, remaining water.

3. The temperature of the culture medium: 30° C., pH: 7.5, cultivation period: 15 days, active microorganisms contained: up to 500 million/gram.

4. Medium to low graded ground phosphate rock, active organic matter and the microbes (after 1st cultivation) of the microorganisms are mixed according to the following formulation, and subjected to fermentation at room temperature for 14 days, resulting in the microbial phosphate fertilizers, which was then subjected to crushing and packing:

| | |
|---|---|
| Ground phosphate rock | 90%; |
| Active organic matter (rapeseed cake: 5%) | 5%; |
| Microbes (after 1st cultivation) | 5%. |

The proportion and parameters of other components and process step are the same as Example 1.

Example 4

Comparative Example 1

Site: Agricultural Science Institute, Chibi City, Hubei Province

Testing agency: Institute of Plant Protection and Soil Science, Academy of Agricultural and Science, Hubei Province Crop: paddy (middle-season rice)

Testing date: Jun. 30, 2007 to Oct. 27, 2007

TABLE 1

The testing treatment and fertilization method of the biological phosphate fertilizer

| Serial No. | Treatment | Nitrogenous fertilizer (kg/mu) | Phosphate fertilizer (kg/mu) | Potassium fertilizer (kg/mu) | Application method |
|---|---|---|---|---|---|
| 1 | CK: only nitrogenous fertilizer and potassium fertilizer | 15.3 | 0 | 11.6 | total basal application of phosphorus fertilizer and potassium fertilizer, basal application of nitrogenous fertilizer: 60%, fertilizer for seed bed: 20%, earing fertilizer: 20% |
| 2 | CK+ 40 kg/mu the biological phosphate fertilizer | 15.3 | 40 | 11.6 | |
| 3 | CK+ 20 kg/mu the biological phosphate fertilizer | 15.3 | 20 | 11.6 | |
| 4 | CK+ 40 kg/mu calcium superphosphate | 15.3 | 40 | 11.6 | |
| 5 | CK+ 40 kg/mu Ground phosphate rock | 15.3 | 40 | 11.6 | |

TABLE 2

Main economic character of middle-season rice with the application of different phosphate fertilizers.

| Treatment | Plant height (cm) | Tiller number (no./plant) | Panicle length (cm) | Total grain number per panicle (panicle/plant) | filled grain number per panicle (grains) | Abortive grain rate (%) | 1000-grain weight (g) |
|---|---|---|---|---|---|---|---|
| 1 | 106.3 | 12.6 | 23.6 | 9.2 | 102.8 | 23.1 | 23.9 |
| 2 | 104.0 | 13.1 | 23.8 | 10.0 | 105.4 | 22.3 | 23.86 |
| 3 | 106.9 | 10.1 | 23.9 | 9.4 | 111.6 | 19.7 | 24.03 |
| 4 | 106.9 | 13.3 | 23.5 | 10.2 | 103.9 | 26.3 | 24.02 |
| 5 | 105.1 | 13.5 | 23.2 | 10.4 | 99.8 | 23.8 | 23.71 |

TABLE 3

Comparison of the yield of middle-season rice with the application of different phosphate fertilizers.

| Treatment | Paddy yield (kg/hm$^2$) | Increase in production compared with the control (kg/hm$^2$) | Increased in production rate (%) |
|---|---|---|---|
| 1 | 7150.4 | 0 | |
| 2 | 7385.4 | 235.1 | 3.29 |
| 3 | 7675.4 | 525 | 7.34 |
| 4 | 7550.3 | 399.9 | 5.59 |
| 5 | 7145.3 | −5.1 | −0.07 |

TABLE 4

The effect of application of different phosphate fertilizers on the phosphorus absorption of middle-season rice.

| Treatment | Phosphorus content of stalk (g/kg) | Stalk yield (kg/hm$^2$) | Total absorption by stalk (kg) | Phosphorus content of seed (g/kg) | Seed yield (kg/hm$^2$) | Total absorption by seed (kg) | Total phosphorus absorption (kg) | Increase in total phosphorus absorption compared with the control (%) |
|---|---|---|---|---|---|---|---|---|
| 1 | 0.649 | 15649.5 | 10.16 | 2 | 7150.4 | 14.30 | 24.46 | — |
| 2 | 0.823 | 15000.0 | 12.35 | 3.1 | 7385.4 | 22.89 | 35.24 | 44.09 |
| 3 | 0.736 | 14374.5 | 10.58 | 2.4 | 7675.4 | 18.42 | 29.00 | 18.58 |
| 4 | 0.813 | 17200.5 | 13.98 | 2.6 | 7550.3 | 19.63 | 33.61 | 37.44 |
| 5 | 0.751 | 18687.0 | 14.03 | 2.7 | 7145.3 | 19.29 | 33.33 | 36.26 |

From the result of the analysis and study on middle season stalk and seeds, it can be seen that the use of the biological phosphate fertilizers of the present invention can improve the total phosphorus absorption of paddy stalk and seeds, and that increase in the total phosphorus absorption of paddy stalk and seeds ranges from 18.58-44.09% compared with the control treatment group where phosphate fertilizers are not used, indicating that the use of the biological phosphate fertilizers of the present invention can improve the efficiency of phosphorus in soil and increase the phosphorus absorption of crops. Meanwhile, the use of 40 kg/mu the biological phosphate fertilizers increases the total phosphorus absorption by 4.85% compared with the group using calcium superphosphate, indicating that the use of the biological phosphate fertilizers of the present invention in soil, which has been applied with chemical phosphate fertilizers for a long time, can produce the effect of increasing yield. The use of the biological phosphate fertilizers exhibits a significant effect in increasing yield. Particularly, the use of 20 kg/mu the biological phosphate fertilizer of the present invention increases the yield by 525 kg/hectare compared with the control treatment group without using phosphate fertilizers, and increases the yield by 125.1 kg/hm² compared with the group using calcium superphosphate. Regardless of the group with 20 kg/mu the biological phosphate fertilizer of the present invention or the group with 40 kg/mu the biological phosphate fertilizer of the present invention, the yield of paddy in both groups is significantly higher than that in the group with ground phosphate rock, indicating that the use of the biological phosphate fertilizers of the present invention can release the slow-release phosphorus in soil, and convert them into a form easier to be used by crops, so as to increase the yield of crop.

Example 5

Comparative Example 2

Site: Corn testing site, crop institute of Academy of Agricultural and Science, Hubei Province
Testing agency: Institute of Plant Protection and Soil Science, Academy of Agricultural, Hubei Province
Crop: corn
Testing date: Aug. 13, 2007 to Nov. 5, 2007

TABLE 1

The tesing treatment and fertilization method of the biological phosphate fertilizers.

| Serial No. | Treatment | Nitrogenous fertilizers (kg/mu) | Phosphate fertilizers (kg/mu) | Potassium fertilizers (kg/mu) | Application method |
|---|---|---|---|---|---|
| 1 | CK: only nitrogenous fertilizer and potassium fertilizer | 15 | 0 | 10 | total basal application of phosphorus-potassium fertilizers, basal application of nitrogenous fertilizer: 60%, fertilizer for seed bed: 20%, earing fertilizer: 20% |
| 2 | CK+ 40 kg/mu the biological phosphate fertilizer | 15 | 40 | 10 | |
| 3 | CK+ 20 kg/mu the biological phosphate fertilizer | 15 | 20 | 10 | |
| 4 | CK+ 40 kg/mu calcium superphosphate | 15 | 40 | 10 | |
| 5 | CK+ 40 kg/mu ground phosphate rock | 15 | 40 | 10 | |

TABLE 2

Yield of Sweet corn subjected to the biological phosphate fertilizer testing.

| Treatment | Fresh corn yield (kg/hm²) | Increase in production compared with the control (%) |
|---|---|---|
| 1. CK: only nitrogenous fertilizer and potassium fertilizer | 6895.4 | |
| 2. CK+ 40 kg/mu the biological phosphate fertilizer | 7366.8 | 6.84 |
| 3. CK+ 20 kg/mu the biological phosphate fertilizer | 7378.8 | 7.01 |
| 4. CK+ 40 kg/mu calcium superphosphate | 7169.4 | 3.98 |
| 5. CK+ 40 kg/mu ground phosphate rock | 6808.9 | −1.25 |

TABLE 3

The effect of application of different phosphate fertilizers on the phosphorus absorption of corn

| Treatment | Phosphorus content of stalk (%) | Stalk yield (kg/hm²) | Total absorption by stalk (kg) | Phosphorus content of seed (%) | Seed yield (kg/hm²) | Total absorption by seed (kg) | Total phosphorus absorption (kg) | Increase in total phosphorus absorption compared with the control (%) |
|---|---|---|---|---|---|---|---|---|
| 1 | 0.2 | 87984.2 | 149.57 | 0.12 | 6895.4 | 8.27 | 157.85 | 0 |
| 2 | 0.17 | 96339.4 | 192.68 | 0.13 | 7366.8 | 9.58 | 202.26 | 28.13 |
| 3 | 0.28 | 82240.4 | 230.27 | 0.10 | 7378.7 | 7.38 | 237.65 | 50.56 |
| 4 | 0.19 | 100091.4 | 190.17 | 0.12 | 7169.4 | 8.60 | 198.78 | 25.93 |
| 5 | 0.13 | 91299.7 | 118.69 | 0.11 | 6808.9 | 7.49 | 126.18 | −20.06 |

TABLE 4

Comparison of the yield of corn with the application of different phosphate fertilizers.

| Treatment | Protein content (%) | Increase in protein content compared with the control (%) |
|---|---|---|
| 1. CK: only nitrogenous fertilizer and potassium fertilizer | 4.44 | 0 |
| 2. CK+ 40 kg/mu the biological phosphate fertilizer | 4.75 | 6.98 |
| 3. CK+ 20 kg/mu the biological phosphate fertilizer | 4.56 | 2.70 |
| 4. CK+ 40 kg/mu calcium superphosphate | 4.25 | −4.28 |
| 5. CK+ 40 kg/mu ground phosphate rock | 4.25 | −4.28 |

From the above table, it can be seen that the use of the biological phosphate fertilizers of the present invention in sweet corn increases the yield by about 7% compared with the control experiment, and exhibits better effects than using calcium superphosphate, and especially in soil continuously applied with chemical phosphate fertilizers, the use of the biological phosphate fertilizers of the present invention gives a dual beneficial effect on crops and environment. The use of the biological phosphate fertilizers of the present invention increases the total phosphorus absorption of corn stalk and seed by 28.13-50.56% compared with the control treatment where phosphate fertilizers are not used, which indicates that the use of the biological phosphate fertilizers of the present invention can improve the efficiency of phosphorus in soil, increase the phosphorus absorption of crops, and that the use of the biological phosphate fertilizers of the present invention increases the total phosphorus absorption by 2.2-24.63% compared with the group using calcium superphosphate, indicating that the use of the biological phosphate fertilizers of the present invention in soil, which has been applied with chemical phosphate fertilizers for a long time, can produce the effect of increasing yield. The use of the biological phosphate fertilizers of the present invention can increase the crude protein content of crops by 2.70-6.98% compared with the control experiment, indicating that not only the biological phosphate fertilizers can improve the phosphorus supply in soil, but they can also improve the nutrient condition of soil as well as the quality of crops.

Example 6

Comparative Example 3

Site: Chongbu village, Sian zhen, Gaoming district, Foshan city, Guangdong province
Host: Chen hao bin
Crop: paddy
See table 1 for comparison of yield, and see table 2 for main economic characters.

TABLE 1

Comparative experiment for yield:

| | Plot Yield (0.1 mu, kg) | | | Average | Yield calculated | Comparative |
|---|---|---|---|---|---|---|
| Type of fertilizers | I | II | III | (kg/plot)) | in mu (kg/mu) | value (+, −) % |
| Microbial phosphate fertilizers | 46.3 | 47.6 | 45.7 | 46.5 | 465 | +4 |
| Calcium superphosphate | 43.8 | 44.9 | 45.3 | 44.7 | 447 | \ |

TABLE 2

Comparative experiment for characters

| Type of fertilizers | Plant height (cm) | Panicle length (cm) | Effective panicle number (10 thousands/mu) | Total grain number per panicle | Filled grain number per panicle | Seed setting rate (%) | 1000-grain weight (g) |
|---|---|---|---|---|---|---|---|
| The microbial phosphate fertilizer according to the present invention | 91.5 | 22.8 | 22.6 | 150 | 124 | 82.7 | 16.0 |
| Calcium superphosphate | 91.1 | 21.9 | 22.2 | 146 | 117 | 80.1 | 15.9 |

The use of the microbial phosphate fertilizers of the present invention in paddy can significantly increase the tiller number, promote the growth of the root system, improve various economic characters, improve the resistance to lodging and relieve the harm of sheath blight. The use of the microbial phosphate fertilizers of the present invention in paddy, in comparison with the group applied with calcium superphosphate, results in an increase in average effective panicle number per plant by 2%, increase in panicle length by 4%, increase in seed setting rate by 3.2%, increase in yield by more than 4% and reduce in the incidence of sheath blight (reduce times of administration of medication by at least one time on a quarterly basis).

Example 7

Comparative Example 4

Site: Jiwei, Dainan Village, Yanghezhen, Gaoming District, Foshan city, Guangdong province
Host: Zhang lianhua
Crop: AU. No. 1 sweet corn See table 1 for comparison of yield, and see table 2 for main economic characters such as stem diameter, plant height

TABLE 1

Comparative experiment for yield unit: kg

| Type of fertilizers | Plot yield (0.1 mu) I | II | III | average | Yield Calculated in mu | Average ear weight |
|---|---|---|---|---|---|---|
| The microbial phosphate fertilizer according to the present invention | 75.3 | 76.9 | 74.0 | 75.4 | 754 | 0.412 |
| Calcium superphosphate | 72.1 | 73.4 | 72.6 | 72.7 | 727 | 0.397 |

TABLE 2

Comparative experiment for characters (such as stem diameter and plant height)

| Type of fertilizers | Stem diameter (cm) | Plant height (cm) | Leaf number (number/plant) | Hollow stem rate (%) | seed absence rate (%) | Bald ear (number/ 0.1 mu) |
|---|---|---|---|---|---|---|
| The microbial phosphate fertilizer according to the present invention | 2.31 | 187 | 13 | 3.2 | 9.7 | 34.0 |
| Calcium superphosphate | 2.10 | 185 | 12 | 3.8 | 11.64 | 38.5 |

The microbial phosphate fertilizers of the present invention can efficiently promote the growth of corn, improve the germination rate and seedling survival rate, prevent premature aging, empty stalk, lack of grain and lodging, increase the stem diameter and leaf number, increase single ear weight and yield, reduce number of bald ear and the occurrence of plant diseases and insect pest, and taste non-fibrous, fresh and sweet. The use of the microbial phosphate fertilizers of the present invention in corn, in comparison with the group applied with calcium superphosphate, results in an increase in stem diameter by 0.1-0.2 cm, increase in leaf number by 1-1.5, increase in single ear weight by 3.6%, reduce in hollow stem rate by 18%, reduce in seed absence rate by 20%, reduce in bald ear by 13%, reduce in the occurrence of leaf spots by 30% and increase in yield by 3.7%.

Example 8

Comparative Example 5

Site: Jiwei, DainanVillage, Yanghezhen, Gaoming District, Foshan city, Guangdong province Host: zhang lianhau Crop: balsam pear See table 1 for comparison of yield, and see table 2 for characters such as fruit setting number and single fruit weight

TABLE 1 yield for each treatment group:

unit: kg

| | Items | | | | | | |
|---|---|---|---|---|---|---|---|
| | Plot yield (0.1 mu) | | | | | Comparative value | |
| Types of fertilizers | I | II | III | average | Calculated per-mu yield | Increase in production | Increase in production rate |
| The microbial phosphate fertilizer of the present invention | 208.7 | 214.7 | 205.7 | 209.5 | 2095 | 81 | 4% |
| Calcium superphosphate | 204.3 | 200.6 | 199.3 | 201.4 | 2014 | \ | \ |

TABLE 2

Comparative experiment for characters, such as fruit setting number and single fruit weight.

| Types of fertilizers | Fruit setting number (number/0.1 mu) | Single fruit weight (g) | Flesh thickness (cm) | Deformed fruit (number/0.1 mu) | Leaf thickness (mm) | Harvest period (day) |
|---|---|---|---|---|---|---|
| The microbial phosphate fertilizer of the present invention | 493 | 425 | 0.54 | 148 | 0.322 | 85 |
| Calcium superphosphate | 483 | 417 | 0.49 | 169 | 0.294 | 77 |

The microbial phosphate fertilizers of the present invention can efficiently improve the growth of balsam pear, increase stem diameter, promote root system well-developed, improve the photosynthesis of leaves and fruit setting rate, increase the thickness and flesh weight, reduce numbers of deformed fruit, increase numbers of classification fruits, extend the harvest period, and reduce the occurrence of blight disease. The use of the microbial phosphate fertilizers of the present invention in balsam pear, in comparison with the group applied with calcium superphosphate, results in an increase in fruit setting rate by 11%, increase in flesh thickness by 0.05 cm, increase in single fruit weight by 8 gram, reduce in number of deformed fruit by 14%, increase in leaf thickness by about 0.03 mm, reduce in wilting disease by 20 to 30%, extend of the harvest period to 7-10 days, and increase in yield by 4%.

What is claimed is:

1. A microorganism, which is *Streptomyces cellulosae* with accession number CGMCC No. 2167; or *Aspergillus versicolor* with accession number CGMCC No. 2171.

2. A microbial phosphate fertilizer, comprising a fermentation product from a microbial composition consisting of the following four microorganisms: *Bacillus subtilis* strain WH2, accession number: CGMCC No. 0395.2; *Bacillus licheniformis* strain WH4, accession number: CGMCC No. 0395.4; *Streptomyces cellulosae* strain WH9, accession number: CGMCC No. 2167; and *Aspergillus versicolor* strain WH13, accession number: CGMCC No. 2171.

3. A microbial phosphate fertilizer of claim 2, wherein said phosphate fertilizer is a fermentation product of the microbes the above microbial composition with ground phosphate rock and active organic matter.

4. A microbial phosphate fertilizer of claim 2, wherein the percentage by weight of the individual microorganisms, based on the total weight of the microbial composition, is as follows:

| (1) Strain WH2: 13-50%; | (2) Strain WH4: 10-45%; |
|---|---|
| (3) Strain WH9: 8-40%; | (4) Strain WH13: 8-37%. |

5. A microbial phosphate fertilizer of claim 3, wherein the percentage by weight of the components is as follows:

| The microbes of the microbial composition | 5-40%; |
|---|---|
| Ground phosphate rock | 20-90%; |
| Active organic matter | 5-40%. |

6. A method for manufacturing a microbial phosphate fertilizer, comprising the following steps of:
   (1) Mixing the four microorganisms, strains WH2, WH4, WH9 and WH13, according to the percentage by weight defined in claim 4 to give the microbial composition;
   (2) Preparing the culture medium for the said microbial composition according to the following percentage by weight:
   Active organic matter: 35-45%; rice bran: 35-45%; soybean powder: 15-17%; milk powder: 1.5-2.5%; sugar: 0.5-1.5%; and remaining water;
   (3) Cultivating the microbes: mixing the culture medium of the microbial composition according to the above formulation with stirring, followed by inoculating the microbial composition at room temperature, cultivating the microbial composition in the culture medium at the temperature ranged from 30° C.-60° C., pH 6.5-7.5 for a period of 5-15 days, and obtaining the microbes of the microbial composition; and
   (4) Mixing the ground phosphate rock, the active organic matter and the microbes of the microbial composition according to the following percentage by weight, fermenting the obtained mixture at room temperature for at least 12 days, and obtaining the microbial phosphate fertilizer:

| Ground phosphate rock | 20-90%; |
|---|---|
| Active organic matter | 5-40%; |
| The microbes of the microbial composition | 5-40%. |

7. A method for manufacturing a microbial phosphate fertilizer of claim 6, wherein said ground phosphate rock has 8% to 28% $P_2O_5$.

* * * * *